United States Patent
Coulthard et al.

(10) Patent No.: US 11,305,046 B2
(45) Date of Patent: *Apr. 19, 2022

(54) SYSTEM FOR PURGING NEGATIVE PRESSURE WOUND THERAPY SYSTEM

(71) Applicant: KCI Licensing, Inc., San Antonio, TX (US)

(72) Inventors: Richard Daniel John Coulthard, Verwood (GB); Kevin W. Bendele, Oldsmar, FL (US); James A. Luckemeyer, San Antonio, TX (US); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 827 days.

This patent is subject to a terminal disclaimer.

(21) Appl. No.: 15/874,126

(22) Filed: Jan. 18, 2018

(65) Prior Publication Data

US 2018/0200415 A1    Jul. 19, 2018

Related U.S. Application Data

(63) Continuation of application No. 13/452,014, filed on Apr. 20, 2012, now Pat. No. 9,907,888.

(60) Provisional application No. 61/477,472, filed on Apr. 20, 2011.

(51) Int. Cl.
*A61M 5/00* (2006.01)
*A61M 1/00* (2006.01)
*A61M 5/32* (2006.01)
*A61M 25/00* (2006.01)
*A61M 35/00* (2006.01)
*A61F 13/00* (2006.01)
*A61F 7/00* (2006.01)

(52) U.S. Cl.
CPC .................. *A61M 1/74* (2021.05); *A61M 1/90* (2021.05)

(58) Field of Classification Search
CPC .......... A61M 5/00; A61M 5/32; A61M 25/00; A61M 35/00; A61M 1/00; A61M 5/178; A61F 13/00; A61F 7/00
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |

(Continued)

FOREIGN PATENT DOCUMENTS

| | | | |
|---|---|---|---|
| AU | 550575 B2 | 3/1986 | |
| AU | 745271 B2 | 3/2002 | |

(Continued)

OTHER PUBLICATIONS

Louis C. Argenta, MD and Michael J. Morykwas, Phd; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Michele M Kidwell
*Assistant Examiner* — Ilya Y Treyger (57) ABSTRACT

Systems and methods for purging a negative pressure wound therapy system.

24 Claims, 3 Drawing Sheets

(56) References Cited

U.S. PATENT DOCUMENTS

| | | |
|---|---|---|
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,599,639 A | 8/1971 | Spotz |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 6,869,275 B2 | 3/2005 | Dante et al. |
| 7,846,141 B2 | 12/2010 | Weston |
| 8,062,273 B2 | 11/2011 | Weston |
| 8,216,198 B2 | 7/2012 | Heagle et al. |
| 8,235,955 B2 | 8/2012 | Blott et al. |
| 8,251,979 B2 | 8/2012 | Malhi |
| 8,257,327 B2 | 9/2012 | Blott et al. |
| 8,273,074 B2 | 9/2012 | Jaeb et al. |
| 8,366,692 B2 | 2/2013 | Weston et al. |
| 8,394,081 B2 | 3/2013 | Locke et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2007/0118096 A1 | 5/2007 | Smith et al. |
| 2007/0179460 A1 | 8/2007 | Adahan |
| 2008/0294127 A1 | 11/2008 | Blott et al. |
| 2009/0275884 A1 | 11/2009 | McNulty et al. |
| 2011/0015587 A1 | 1/2011 | Tumey et al. |
| 2014/0163491 A1 | 6/2014 | Schuessler et al. |
| 2015/0080788 A1 | 3/2015 | Blott et al. |

FOREIGN PATENT DOCUMENTS

| | | |
|---|---|---|
| AU | 755496 B2 | 12/2002 |
| CA | 2005436 A1 | 6/1990 |
| CN | 1732028 A | 2/2006 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |

(56) References Cited

FOREIGN PATENT DOCUMENTS

| WO | 93/009727 A1 | 5/1993 |
|---|---|---|
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2008130689 A1 | 10/2008 |
| WO | 2010017484 A2 | 2/2010 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

FIG. 3

SYSTEM FOR PURGING NEGATIVE PRESSURE WOUND THERAPY SYSTEM

CROSS-REFERENCE TO RELATED APPLICATIONS

This application is a continuation of U.S. patent application Ser. No. 13/452,014, filed Apr. 20, 2012, which claims priority to U.S. Provisional Patent Application No. 61/477,472, filed Apr. 20, 2011, the entire contents of which are incorporated herein by reference.

BACKGROUND OF THE INVENTION

Field of the Invention

This invention relates to a system and method for purging a negative pressure wound therapy system.

Description of the Related Art

The referenced shortcomings are not intended to be exhaustive, but rather are among many that tend to impair the effectiveness of previously known techniques in purging a negative pressure wound therapy (NPWT) system. However, those mentioned here are sufficient to demonstrate that the methodologies appearing in the art have not been satisfactory and that a significant need exists for the techniques described and claimed in this disclosure.

Advanced NPWT devices and systems use multiple fluid channels to provide therapeutic negative pressure, transport wound products (liquid and solid) and monitor the applied negative pressure close to the wound site (via additional tubing lumens, typically). During this process several problems can be encountered, which can cause therapy to be interrupted or accuracy to be compromised.

For example, the therapy line may be blocked by highly viscous fluids, solid matter, or wound products coagulating in the line due to long residency time when flow is restricted under low leak conditions. In addition, the wound pressure sensing line may be blocked by wound fluid and/or instillation fluid.

Current practice in some advanced NPWT products is to periodically vent the wound pressure sensing line to atmosphere (near the pump/sensor end of the line), which allows the vacuum in the wound dressing to pull a short burst of air into the wound and thus attempt to clear a blockage in the sensing lumen(s). However, when instillation therapy is used in conjunction with NPWT, there can be little or no vacuum at the wound site. Moreover, there is a tendency for practitioners to over-fill the wound with instillation fluid, which can drive instillation fluid up the wound pressure sensing lines and thereby prevent accurate sensing of wound pressure until the fluid in the wound pressure sensing lumen(s) is removed. Wound pressure sensing is accurate only if there is a clear air path between the sensor and wound site, and wound pressure sensing will be degraded if there are slugs of fluid in the sensing lines.

SUMMARY OF THE INVENTION

From the foregoing discussion, it should be apparent that a need exists for effective systems and methods for purging an NPWT system.

Systems and methods are presented for purging an NPWT system. The method in the disclosed embodiments substantially includes the steps necessary to carry out the functions presented above with respect to the operation of the described system.

Certain embodiments comprise a system for purging a negative pressure wound therapy system. In particular embodiments, the system may comprise a negative pressure source comprising an inlet and an outlet, where the inlet is configured for fluid communication with a wound therapy dressing via a first conduit, and the outlet is configured for fluid communication with a wound therapy dressing via a second conduit. Particular embodiments may also comprise a diverter valve coupled to the second conduit, where the diverter valve is configured to allow a fluid flow from the negative pressure source to atmosphere when the diverter valve is in a first position and where the diverter valve is configured to allow a fluid flow from the negative pressure source to a wound therapy dressing through the second conduit when the diverter valve is in a second position.

In particular embodiments, the diverter valve can be configured to prevent fluid flow from the negative pressure source to a wound therapy dressing through the second conduit when the diverter valve is in the first position. In specific embodiments, the diverter valve can be configured to prevent a fluid flow from the negative pressure source to atmosphere when the diverter valve is in the second position. Certain embodiments may further comprise a pressure sensor configured to detect the pressure in the second conduit. Particular embodiments may also comprise a reservoir in fluid communication with the first and second conduits.

In specific embodiments, the diverter valve may be a piezoelectric valve. In particular embodiments, the negative pressure source can comprise a vacuum pump. Certain embodiments may further comprise a pump configured to deliver instillation fluid to a wound therapy dressing.

Particular embodiments may comprise a method of purging a negative pressure wound therapy system. In certain embodiments, the method can comprise operating a negative pressure source coupled to a wound therapy dressing, where: the negative pressure source comprises an inlet and an outlet; the inlet is in fluid communication with the wound therapy dressing via a first conduit; the outlet is in fluid communication with the wound therapy dressing via a second conduit; the second conduit is in fluid communication with a diverter valve; the diverter valve is configured to allow a fluid flow from the negative pressure source to atmosphere when the diverter valve is in a first position; and the diverter is configured to allow a fluid flow from the negative pressure source to the wound therapy dressing through the second conduit when the diverter valve is in a second position. Certain embodiments comprise operating the negative pressure source to provide a negative pressure at the wound therapy dressing with the diverter valve in the first position; and manipulating the diverter valve from the first position to the second position.

In particular embodiments, the fluid flow can purge an obstruction from either the first or second conduit when the diverter valve is in the second position. Certain embodiments can further comprise detecting the pressure of the first conduit via a first pressure sensor. Specific embodiments further comprise detecting the pressure of the second conduit via a second pressure sensor. In certain embodiments, manipulating the diverter valve from the first position to the second position can be performed when the pressure of the first or second pressure sensor reaches a first predetermined value. In particular embodiments, manipulating the diverter valve can be performed automatically by an electronic control circuit. In certain embodiments, the diverter valve can comprise a piezoelectric valve.

In particular embodiments, the negative pressure source can comprise a vacuum pump. Particular embodiments, can further comprise manipulating the diverter valve from the second position back to the first position. Certain embodiments further comprise repeatedly manipulating the diverter valve between the first and second positions.

Specific embodiments further comprise detecting the pressure in the first or second conduit, and wherein manipulating the diverter valve from the second position back to the first position is performed when the pressure in the first or second conduit reaches a second predetermined value.

20. A tangible computer readable medium comprising computer readable code that, when executed by a computer, causes the computer to perform operations comprising the steps set forth in claims 9-19.

Exemplary embodiments of the present disclosure comprise a valve placed at the outlet (e.g., positive pressure side) of a negative pressure source in an NPWT system. In certain embodiments, the valve can either channel the flow to atmosphere (e.g, via a silencing device) or divert some or all of the flow to the wound pressure sensing channel. During normal negative pressure therapy, the valve can be set to the exhaust position. When a blockage is detected or suspected (or during instillation) the negative pressure in the system can be relieved and the valve can be used in combination with the negative pressure source to circulate air through a sensing channel (thus clearing any blockage in the sensing lumen) to the connector pad of a wound dressing and then back through the therapy line and canister/reservoir.

In exemplary embodiments, air is not added to the system and the dressing will not become pressurized. Matter or obstructions caught in the sensing or therapy channels can eventually be collected in the reservoir, which may incorporate a fluid/air separation membrane.

The level of pressure utilized in exemplary embodiments can be varied depending on the conditions. A blockage may require a higher level of pressure whereas maintaining open sensing lines during instillation may require less pressure.

In certain embodiments the reservoir can be vented to atmosphere (using an additional valve, not shown) during the instillation cycle, to avoid pulling the instillation fluid from the wound site. The outlet valve can be used to allow the negative pressure source (e.g., a vacuum pump) to pull atmospheric air through the pump and provide a slight positive pressure through the wound pressure sensing lines to prevent instillation fluid from entering the lines.

In certain embodiments utilizing a multiple-patient-use therapy device, microbial filters may be incorporated to the system for recirculating air through the multiple-patient-use negative pressure source. Alternatively, the negative pressure source exhaust could be used to drive an isolation diaphragm to indirectly pump positive pressure into the wound dressing from a filtered ambient source.

Exemplary embodiments of the present disclosure comprise numerous advantages over existing systems. For example, exemplary embodiments are configured to clear fluid lines without applying high pressures to the wound site, as well as to avoid the use of a high negative pressure pump source to try to clear an obstruction. Furthermore, exemplary embodiments are configured to decrease the likelihood of fluid entering a pressure sensing line during instillation. Finally, exemplary embodiments are configured to regulate the air recirculation path (e.g. with a variable valve at the pump exhaust), in order to maintain wound vacuum in the presence of dressing leaks.

Other features and associated advantages will become apparent with reference to the following detailed description of specific embodiments in connection with the accompanying drawings.

The term "coupled" is defined as connected, although not necessarily directly, and not necessarily mechanically. The terms "a" and "an" are defined as one or more unless this disclosure explicitly requires otherwise.

The term "substantially" and its variations are defined as being largely but not necessarily wholly what is specified as understood by one of ordinary skill in the art, and in one non-limiting embodiment "substantially" refers to ranges within 10%, preferably within 5%, more preferably within 1%, and most preferably within 0.5% of what is specified.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Various features and advantageous details are explained more fully with reference to the nonlimiting embodiments that are illustrated in the accompanying drawings and detailed in the following description. Descriptions of well-known starting materials, processing techniques, components, and equipment are omitted so as not to unnecessarily obscure the invention in detail. It should be understood, however, that the detailed description and the specific examples, while indicating embodiments of the invention, are given by way of illustration only, and not by way of limitation. Various substitutions, modifications, additions, and/or rearrangements within the spirit and/or scope of the underlying inventive concept will become apparent to those skilled in the art from this disclosure.

In the following description, numerous specific details are provided, such as examples of programming, software modules, user selections, network transactions, database queries, database structures, hardware modules, hardware circuits, hardware chips, etc., to provide a thorough understanding of the present embodiments. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Figure 1:
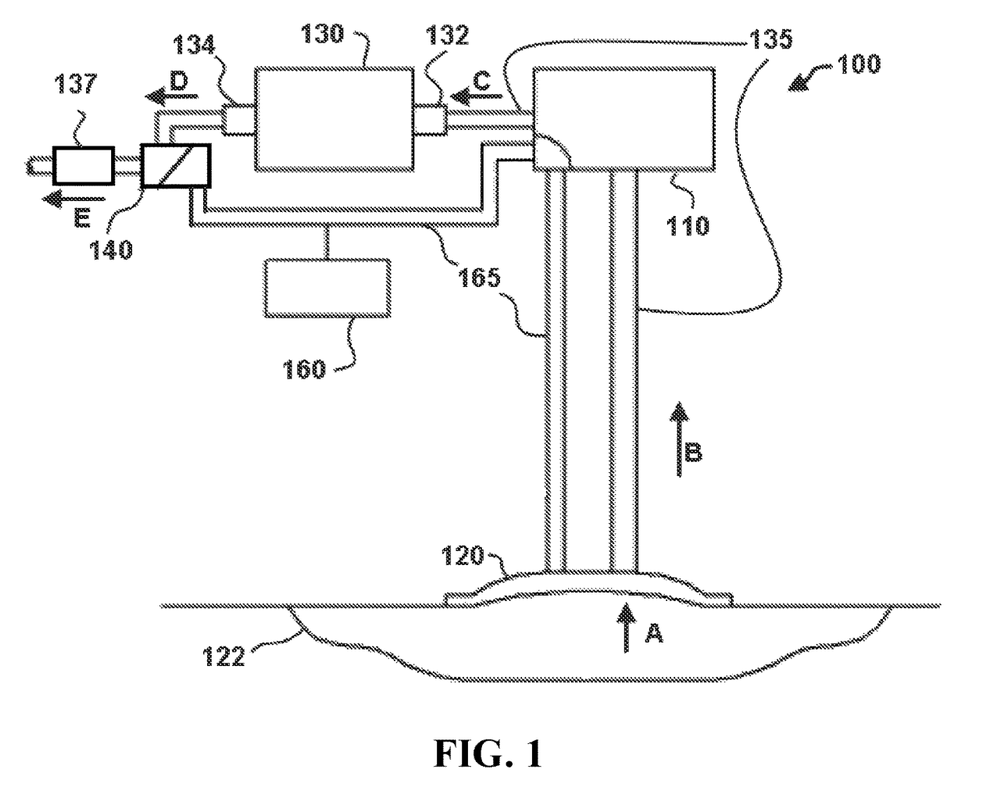
FIG. 1 is a schematic block diagram illustrating one embodiment of a system purging an NPWT system in a first mode of operation.
Figure 2:
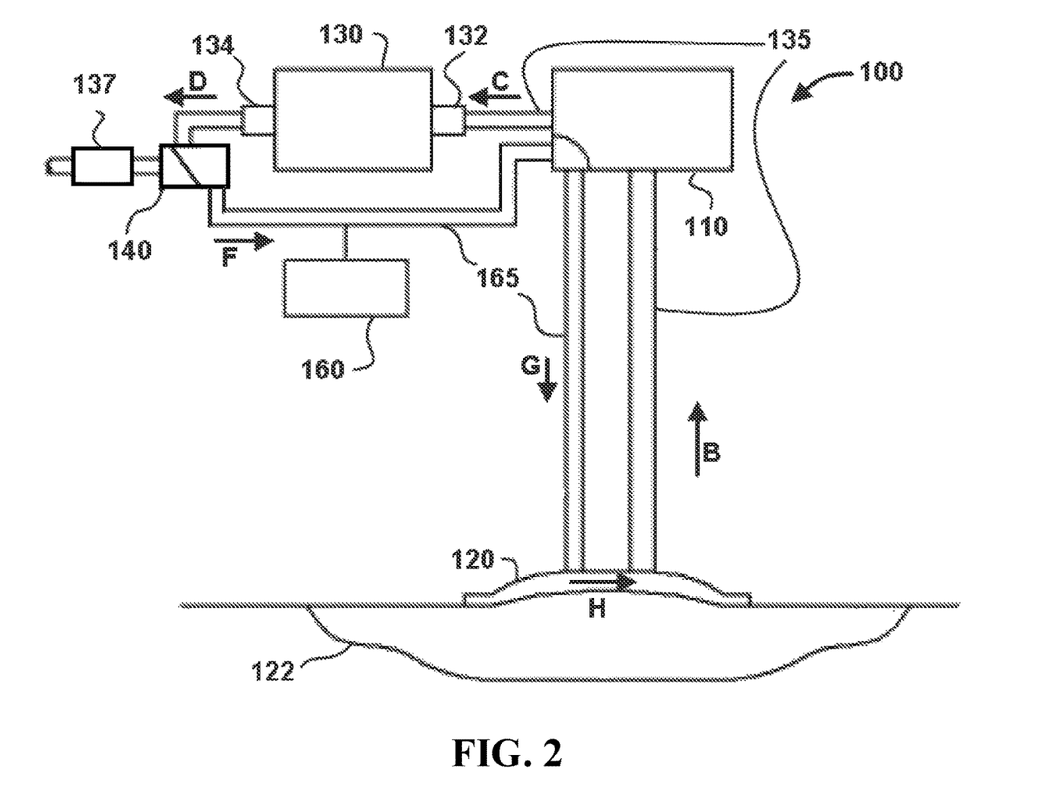
FIG. 2 is a schematic block diagram of the embodiment of FIG. 1 in a second mode of operation.

FIGS. 1-2 illustrate one embodiment of a system 100 for purging and providing fluid delivery to a negative pressure wound therapy system. In the exemplary embodiment shown, system 100 includes a reservoir 110, a wound dressing 120 coupled to a wound 122, and a negative pressure source 130 comprising an inlet 132 and an outlet 134. In this embodiment, negative pressure source 130 is coupled to, and in fluid communication with, reservoir 110 and wound dressing 120 via first conduit 135. During operation of system 100, reservoir 110 can be used to capture wound fluids.

In particular exemplary embodiments, negative pressure source 130 may comprise a diaphragm vacuum pump, a piezoelectric pump, or a micro-pump, including those sold under the Vortis™ brand name. In certain embodiments, system 100 may also comprise a filter or muffler 137 coupled to negative pressure source 130 to reduce the operating noise of negative pressure source 130 and/or filter air exiting negative pressure source 130.

Certain exemplary embodiments, may also comprise a fluid flow device (not shown), e.g. comprise a peristaltic, centrifugal or other suitable pump, to provide instillation fluid to wound dressing 120. In other exemplary embodiments, a fluid flow device may comprise a gravity feed system instead of (or in conjunction with) a pump to deliver fluid to wound dressing 120.

The exemplary embodiment shown in FIGS. 1-2 also comprises a pressure sensor 160 coupled to, and in fluid communication with, wound dressing 120 via a second conduit 165. In certain embodiments, portions of second conduit 165 may be referred to as a "pressure sensing line", and portions of first conduit 135 may be referred to as a "therapy line".

The disclosed embodiment further comprises a diverter valve 140 configured for manipulation from a first position to a second position. In certain embodiments, diverter valve 140 may comprise a piezoelectric valve or solenoid valve. In particular embodiments, diverter valve 140 may be manipulated automatically via an electronic control circuit. In certain embodiments, valve 140 may be a manually operated valve, and system 100 may comprise an input control for valve 140.

In this exemplary embodiment, diverter valve 140 is configured to allow a fluid flow (e.g. air flow) from the negative pressure source to atmosphere when diverter valve 140 is in the first position. In addition, diverter valve 140 is configured to allow a fluid flow (e.g., air flow) from the negative pressure source to the wound therapy dressing (via second conduit 165) when the diverter valve is in a second position. In certain embodiments, diverter valve 140, can be placed in a plurality of positions from fully open to fully closed, as well as partially-open intermediate positions between the fully open and fully closed positions.

Referring specifically to FIG. 1, arrows A-E indicate the direction of fluid flow (e.g. air and/or instillation fluid) when diverter valve 140 is in the first position and negative pressure source 130 activated. As shown in this embodiment, fluid flows from wound 122 through wound dressing 120 (indicated by arrow A), into conduit 135 (arrow B) and then reservoir 110. From reservoir 110, fluid flows into inlet 132 of negative pressure source 130 (indicated by arrow C) and exits from outlet 134 (indicated by arrow D). At this point in the system, diverter valve 140 directs the fluid flow to atmosphere (indicated by arrow E) through filter or muffler 137. With diverter valve 140 in the position shown in FIG. 1, fluid flow is restricted from conduit 165 and pressure sensor 160.

Referring now specifically to FIG. 2, arrows B-G indicate the direction of fluid flow (e.g. air and/or instillation fluid) when diverter valve 140 is in the second position and negative pressure source 130 activated. Similar to the embodiment shown in FIG. 1, fluid flows from wound dressing 120 through conduit 135 (indicated by arrow B) and into reservoir 110. From reservoir 110, fluid (e.g. air) flows into inlet 132 of negative pressure source 130 (indicated by arrow C) and exits from outlet 134 (indicated by arrow D). At this point in the system, diverter valve 140 has been moved from the first position shown in FIG. 1 to the second position shown in FIG. 2. In the second position, diverter valve 140 directs fluid flow to conduit 165, pressure sensor 160 and reservoir 110 (indicated by arrow F). From this point, fluid flow is directed to wound dressing 120 (indicated by arrow G). When fluid flow reaches wound dressing 120, it then travels through wound insert 120 to conduit 135 (indicated by arrow H). At this stage, fluid flow enters first conduit 135 (indicated by arrow B) and the fluid flow cycle is repeated.

In exemplary embodiments, the fluid flow cycle shown and described in FIG. 2 can be continued for the desired duration. Wound dressing 120, or other components such as conduits 135 and 165, can be cleared of obstructions due to the changes in fluid flow and/or pressure resulting from the manipulation of diverter valve 140. In exemplary embodiments, obstructions cleared from system components can be collected in reservoir 110, allowing a clear path for fluid flow through system 100. It is understood that certain embodiments may not include certain components illustrated in FIGS. 1 and 2, e.g. reservoir 110 or pressure sensor 160. In certain embodiments, negative pressure source 130 may comprise an internal reservoir configured to collect obstructions cleared from system 100.

In certain embodiments, diverter valve 140 can be manipulated back and forth between the positions shown in FIGS. 1 and 2 in order to cyclically vary the fluid flow and/or pressure throughout system 100. In certain embodiments, diverter valve 140 can be held in an intermediate position to maintain a low flow of air through conduit 165.

The schematic flow chart diagrams that follow are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method.

Additionally, the order in which a particular method occurs may or may not strictly adhere to the order of the corresponding steps shown.

Figure 3:
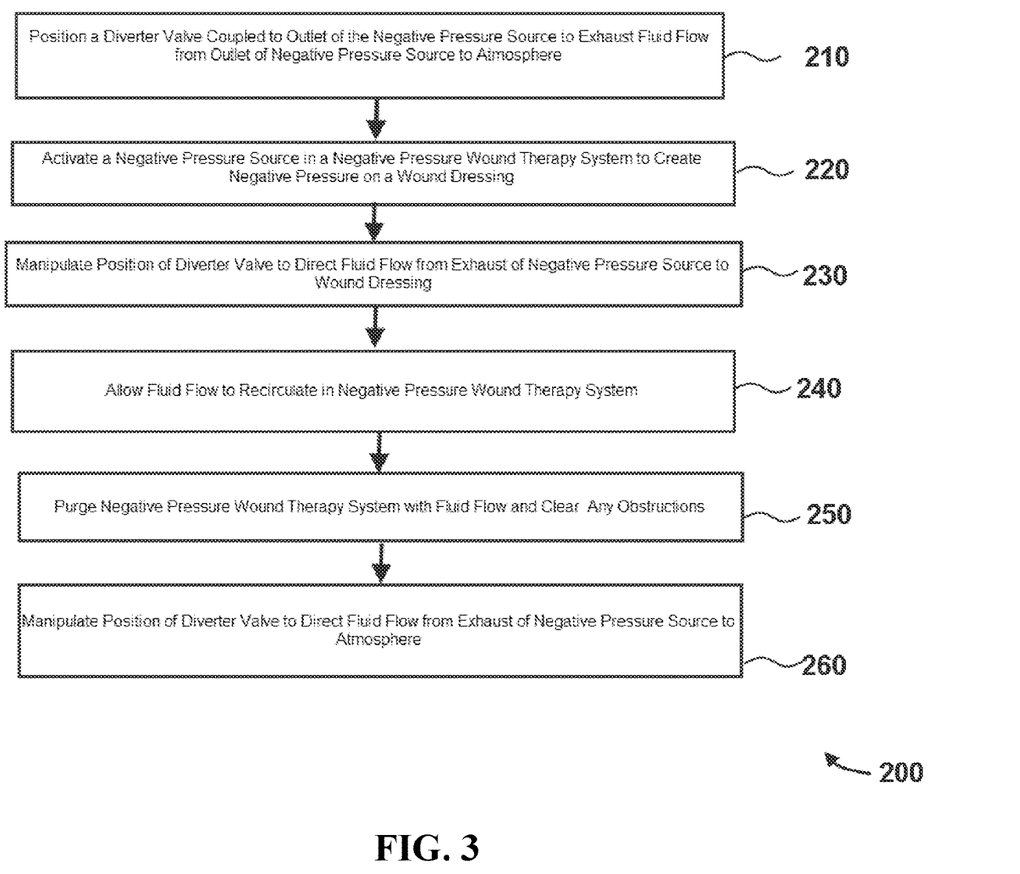
FIG. 3 is a flowchart illustrating a series of steps that can be performed in one embodiment of a method for purging an NPWT system.

FIG. 3 illustrates one embodiment of a method 200 for purging a negative pressure wound therapy system. Method 200 comprises a series of steps that may be executed for the operation of an exemplary system according to this disclosure. Certain embodiments may comprise a tangible computer readable medium comprising computer readable code that, when executed by a computer, causes the computer to perform operations comprising the steps disclosed in FIG. 3.

Step 210 comprises positioning a diverter valve coupled to the outlet of the negative pressure source to exhaust fluid flow from the outlet of the negative pressure source to atmosphere. In this exemplary embodiment, step 220 comprises activating a negative pressure source in a negative pressure wound therapy system to create negative pressure on a wound dressing. Step 230 comprises manipulating the position of the diverter valve to direct fluid flow from the exhaust of the negative pressure system to the wound dressing. Step 240 comprises allowing fluid flow to recirculate in the negative pressure wound therapy system. Step 250 comprises manipulating the position of the diverter valve to direct fluid from the exhaust of the negative pressure source to the wound dressing to purge any blockage in the pressure sensor line. The control cycle repeats as needed with Step 230 to maintain desired wound vacuum.

All of the methods disclosed and claimed herein can be made and executed without undue experimentation in light of the present disclosure. While the systems and methods have been described in terms of preferred embodiments, it will be apparent to those of skill in the art that variations may be applied to the methods and in the steps or in the sequence of steps of the method described herein without departing from the concept, spirit and scope of the invention. In addition, modifications may be made to the disclosed system, and components may be eliminated or substituted for the components described herein where the same or similar results would be achieved. For example, rather than a diverter valve on the outlet of the negative pressure source, one or more check valves could be utilized along with a negative pressure source configured to provide reversible fluid flow.

All such similar substitutes and modifications apparent to those skilled in the art are deemed to be within the spirit, scope, and concept of the invention as defined by the appended claims.

What is claimed is:

1. A system for purging a negative pressure wound therapy system, the system comprising:
a negative pressure source comprising an inlet and an outlet, wherein:
the inlet is configured for fluid communication with a wound therapy dressing via a first conduit; and
the outlet is configured for fluid communication with the wound therapy dressing via a second conduit; and
a diverter valve coupled to the second conduit, wherein the diverter valve is configured to allow a fluid flow from the negative pressure source to atmosphere when the diverter valve is in a first position, wherein the diverter valve is configured to prevent fluid flow from the negative pressure source to the wound therapy dressing through the second conduit when the diverter valve is in the first position, and wherein the diverter valve is configured to allow a fluid flow from the negative pressure source to a wound therapy dressing through the second conduit when the diverter valve is in a second position.

2. The system of claim 1 wherein the diverter valve is configured to prevent a fluid flow from the negative pressure source to atmosphere when the diverter valve is in the second position.

3. The system of claim 1 further comprising a pressure sensor configured to detect the pressure in the second conduit.

4. The system of claim 1 further comprising a reservoir in fluid communication with the first and second conduits.

5. The system of claim 1 wherein the diverter valve is a piezoelectric valve.

6. The system of claim 1 wherein the negative pressure source comprises a vacuum pump.

7. The system of claim 1 further comprising a pump configured to deliver instillation fluid to the wound therapy dressing.

8. A method of purging a negative pressure wound therapy system, the method comprising:
operating a negative pressure source coupled to a wound therapy dressing, wherein:
the negative pressure source comprises an inlet and an outlet;
the inlet is in fluid communication with the wound therapy dressing via a first conduit;
the outlet is in fluid communication with the wound therapy dressing via a second conduit;
the second conduit is in fluid communication with a diverter valve;
the diverter valve is configured to allow a fluid flow from the negative pressure source to atmosphere when the diverter valve is in a first position;
the diverter valve is configured to prevent fluid flow from the negative pressure source to the wound therapy dressing through the second conduit when the diverter valve is in the first position; and
the diverter valve is configured to allow a fluid flow from the negative pressure source to the wound therapy dressing through the second conduit when the diverter valve is in a second position;
operating the negative pressure source to provide a negative pressure at the wound therapy dressing with the diverter valve in the first position; and
manipulating the diverter valve from the first position to the second position.

9. The method of claim 8 wherein the fluid flow purges an obstruction from either the first or second conduit when the diverter valve is in the second position.

10. The method of claim 8 further comprising detecting the pressure of the first conduit via a first pressure sensor.

11. The method of claim 10 further comprising detecting the pressure of the second conduit via a second pressure sensor.

12. The method of claim 11 wherein manipulating the diverter valve from the first position to the second position is performed when the pressure of the first or second pressure sensor reaches a first predetermined value.

13. The method of claim 12 wherein manipulating the diverter valve is performed automatically by an electronic control circuit.

14. The method of claim 8 wherein the diverter valve comprises a piezoelectric valve.

15. The method of claim 8 wherein the negative pressure source comprises a vacuum pump.

16. The method of claim 8 further comprising manipulating the diverter valve from the second position back to the first position.

17. The method of claim 16 further comprising repeatedly manipulating the diverter valve between the first and second positions.

18. The method of claim 16, further comprising detecting the pressure in the first or second conduit, and wherein manipulating the diverter valve from the second position back to the first position is performed when the pressure in the first or second conduit reaches a second predetermined value.

19. A system for purging a negative pressure wound therapy system, the system comprising:
   a reservoir;
   a negative pressure source comprising an inlet for negative pressure and an outlet for positive pressure, wherein:
      the inlet is configured for fluid communication with a wound therapy dressing via a first conduit and the reservoir; and
      the outlet is configured for fluid communication with the wound therapy dressing through the reservoir via a second conduit; and
   a diverter valve directly coupled to the outlet and coupled to the second conduit, wherein the diverter valve is configured to allow a fluid flow from the outlet to atmosphere when the diverter valve is in a first position, wherein the diverter valve is configured to prevent fluid flow from the negative pressure source to the wound therapy dressing through the second conduit when the diverter valve is in the first position, and wherein the diverter valve is configured to allow a fluid flow from the outlet to the wound therapy dressing through the second conduit when the diverter valve is in a second position.

20. The system of claim 19, wherein the diverter valve is configured to prevent a fluid flow from the negative pressure source to atmosphere when the diverter valve is in the second position.

21. The system of claim 19, further comprising a pressure sensor configured to detect the pressure in the second conduit.

22. The system of claim 19, wherein the diverter valve is a piezoelectric valve.

23. The system of claim 19, wherein the negative pressure source comprises a vacuum pump.

24. The system of claim 19, further comprising a pump configured to deliver instillation fluid to a wound therapy dressing.

* * * * *